(12) United States Patent
Coulthard et al.

(10) Patent No.: US 10,279,088 B2
(45) Date of Patent: May 7, 2019

(54) DELIVERY-AND-FLUID-STORAGE BRIDGES FOR USE WITH REDUCED-PRESSURE SYSTEMS

(71) Applicant: KCI Licensing, Inc., San Antonio, TX (US)

(72) Inventors: Richard Daniel John Coulthard, Verwood (GB); Christopher Brian Locke, Bournemouth (GB); Shannon C. Ingram, Bulverde, TX (US); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 975 days.

(21) Appl. No.: 14/334,510

(22) Filed: Jul. 17, 2014

(65) Prior Publication Data

US 2014/0330227 A1    Nov. 6, 2014

Related U.S. Application Data

(63) Continuation of application No. 13/046,164, filed on Mar. 11, 2011, now Pat. No. 8,814,842.
(Continued)

(51) Int. Cl.
*A61M 1/00* (2006.01)
*A61F 13/02* (2006.01)

(52) U.S. Cl.
CPC ......... *A61M 1/009* (2014.02); *A61F 13/0206* (2013.01); *A61F 13/0216* (2013.01);
(Continued)

(58) Field of Classification Search
CPC combination set(s) only.
See application file for complete search history.

(56) References Cited

U.S. PATENT DOCUMENTS

| 1,355,846 A | 10/1920 | Rannells |
| 1,944,834 A | 1/1934 | Bennett |

(Continued)

FOREIGN PATENT DOCUMENTS

| AU | 550575 A1 | 3/1986 |
| AU | 745271 | 4/1999 |

(Continued)

OTHER PUBLICATIONS

European Search Report for corresponding Application No. 15192606.0 dated Feb. 24, 2016.
(Continued)

*Primary Examiner* — Tatyana Zalukaeva
*Assistant Examiner* — Guy K Townsend

(57) ABSTRACT

Systems, methods, and apparatuses are presented that facilitate the provision of reduced pressure to a tissue site by using a delivery-and-fluid-storage bridge, which separates liquids and gases and provides a flow path for reduced pressure. In one instance, a delivery-and-fluid-storage bridge includes a delivery manifold for delivering reduced pressure to a treatment manifold at the tissue site and an absorbent layer proximate the delivery manifold adapted to receive and absorb liquids. The delivery manifold and the absorbent layer are encapsulated in an encapsulating pouch. A first aperture is formed proximate a first longitudinal end of the delivery-and-fluid-storage bridge for fluidly communicating reduced pressure to the delivery manifold from a reduced-pressure source, and a second aperture is formed on a patient-facing side of the delivery-and-fluid-storage bridge. Reduced pressure is transferred to the tissue site via the second aperture. Other systems, apparatuses, and methods are disclosed.

66 Claims, 7 Drawing Sheets

Related U.S. Application Data

(60) Provisional application No. 61/314,299, filed on Mar. 16, 2010.

(52) U.S. Cl.
CPC ...... *A61F 13/0223* (2013.01); *A61F 13/0289* (2013.01); *A61M 1/0023* (2013.01); *A61M 1/0086* (2014.02); *A61M 1/0088* (2013.01); *A61M 2205/18* (2013.01); *A61M 2205/3379* (2013.01); *A61M 2205/75* (2013.01); *A61M 2205/7536* (2013.01); *A61M 2207/00* (2013.01); *Y10T 29/49826* (2015.01)

(56) References Cited

U.S. PATENT DOCUMENTS

| | | | | |
|---|---|---|---|---|
| 2,547,758 | A * | 4/1951 | Keeling | A61F 5/453 604/174 |
| 2,552,664 | A | 5/1951 | Burdine | |
| 2,632,443 | A | 3/1953 | Lesher | |
| 2,682,873 | A * | 7/1954 | Evans | A61F 13/00029 602/42 |
| 2,860,081 | A | 11/1958 | Eiken | |
| 2,910,763 | A * | 11/1959 | Lauterbach | D04H 1/06 128/DIG. 14 |
| 2,969,057 | A | 1/1961 | Simmons | |
| 3,066,672 | A | 12/1962 | Crosby, Jr. et al. | |
| 3,172,808 | A | 3/1965 | Baumann et al. | |
| 3,183,116 | A | 5/1965 | Schaar | |
| 3,367,332 | A | 2/1968 | Groves | |
| 3,376,868 | A | 4/1968 | Mondiadis | |
| 3,520,300 | A * | 7/1970 | Flower, Jr. | A61M 1/008 433/91 |
| 3,568,675 | A | 3/1971 | Harvey | |
| 3,648,692 | A | 3/1972 | Wheeler | |
| 3,682,180 | A | 8/1972 | McFarlane | |
| 3,742,952 | A | 7/1973 | Magers et al. | |
| 3,774,611 | A | 11/1973 | Tussey et al. | |
| 3,777,016 | A | 12/1973 | Gilbert | |
| 3,779,243 | A | 12/1973 | Tussey et al. | |
| 3,826,254 | A | 7/1974 | Mellor | |
| 3,852,823 | A | 12/1974 | Jones | |
| 3,903,882 | A | 9/1975 | Augurt | |
| 3,967,624 | A | 7/1976 | Milnamow | |
| 3,983,297 | A | 9/1976 | Ono et al. | |
| 4,060,081 | A | 11/1977 | Yannas et al. | |
| 4,080,970 | A | 3/1978 | Miller | |
| 4,096,853 | A * | 6/1978 | Weigand | A61M 25/02 600/431 |
| 4,139,004 | A | 2/1979 | Gonzalez, Jr. | |
| 4,141,361 | A | 2/1979 | Snyder | |
| 4,163,822 | A | 8/1979 | Walter | |
| 4,165,748 | A | 8/1979 | Johnson | |
| 4,184,510 | A | 1/1980 | Murry et al. | |
| 4,233,969 | A | 11/1980 | Lock et al. | |
| 4,245,630 | A | 1/1981 | Lloyd et al. | |
| 4,256,109 | A | 3/1981 | Nichols | |
| 4,261,363 | A * | 4/1981 | Russo | A61M 25/02 128/200.26 |
| 4,275,721 | A | 6/1981 | Olson | |
| 4,284,079 | A | 8/1981 | Adair | |
| 4,297,995 | A | 11/1981 | Golub | |
| 4,333,468 | A * | 6/1982 | Geist | A61M 25/02 128/DIG. 26 |
| 4,360,015 | A | 11/1982 | Mayer | |
| 4,373,519 | A * | 2/1983 | Errede | A61F 13/00046 128/DIG. 21 |
| 4,382,441 | A * | 5/1983 | Svedman | A61F 13/00068 604/114 |
| 4,392,853 | A * | 7/1983 | Muto | A61M 25/0111 128/DIG. 26 |
| 4,392,858 | A | 7/1983 | George et al. | |
| 4,414,970 | A | 11/1983 | Berry | |
| 4,419,097 | A | 12/1983 | Rowland | |
| 4,465,485 | A | 8/1984 | Kashmer et al. | |
| 4,475,909 | A | 10/1984 | Eisenberg | |
| 4,480,638 | A * | 11/1984 | Schmid | A61F 5/34 128/118.1 |
| 4,525,166 | A | 6/1985 | Leclerc | |
| 4,525,374 | A | 6/1985 | Vaillancourt | |
| 4,529,402 | A | 7/1985 | Weilbacher et al. | |
| 4,540,412 | A | 9/1985 | Van Overloop | |
| 4,543,100 | A | 9/1985 | Brodsky | |
| 4,548,202 | A | 10/1985 | Duncan | |
| 4,551,139 | A | 11/1985 | Plaas et al. | |
| 4,569,348 | A | 2/1986 | Hasslinger | |
| 4,600,146 | A | 7/1986 | Ohno | |
| 4,605,399 | A | 8/1986 | Weston et al. | |
| 4,608,041 | A | 8/1986 | Nielsen | |
| 4,640,688 | A | 2/1987 | Hauser | |
| 4,655,754 | A | 4/1987 | Richmond et al. | |
| 4,664,652 | A | 5/1987 | Weilbacher | |
| 4,664,662 | A | 5/1987 | Webster | |
| 4,710,165 | A | 12/1987 | McNeil et al. | |
| 4,715,857 | A | 12/1987 | Juhasz et al. | |
| 4,733,659 | A | 3/1988 | Edenbaum et al. | |
| 4,743,232 | A | 5/1988 | Kruger | |
| 4,753,230 | A * | 6/1988 | Carus | A61F 13/00 602/47 |
| 4,758,220 | A | 7/1988 | Sundblom et al. | |
| 4,787,888 | A | 11/1988 | Fox | |
| 4,826,494 | A | 5/1989 | Richmond et al. | |
| 4,832,008 | A | 5/1989 | Gilman | |
| 4,838,883 | A | 6/1989 | Matsuura | |
| 4,840,187 | A | 6/1989 | Brazier | |
| 4,848,364 | A * | 7/1989 | Bosman | A61F 2/0063 128/849 |
| 4,863,449 | A | 9/1989 | Therriault et al. | |
| 4,871,611 | A | 10/1989 | LeBel | |
| 4,872,450 | A | 10/1989 | Austad | |
| 4,878,901 | A | 11/1989 | Sachse | |
| 4,897,081 | A * | 1/1990 | Poirier | A61L 29/041 128/DIG. 26 |
| 4,906,233 | A | 3/1990 | Moriuchi et al. | |
| 4,906,240 | A * | 3/1990 | Reed | A61F 13/023 602/46 |
| 4,919,654 | A * | 4/1990 | Kalt | A61M 25/02 128/DIG. 26 |
| 4,930,997 | A * | 6/1990 | Bennett | A61M 1/0019 417/410.1 |
| 4,941,882 | A | 7/1990 | Ward et al. | |
| 4,953,565 | A | 9/1990 | Tachibana et al. | |
| 4,961,493 | A | 10/1990 | Kaihatsu | |
| 4,969,880 | A | 11/1990 | Zamierowski | |
| 4,981,474 | A | 1/1991 | Bopp et al. | |
| 4,985,019 | A * | 1/1991 | Michelson | A61B 6/12 128/DIG. 26 |
| 4,995,382 | A | 2/1991 | Lang et al. | |
| 4,996,128 | A * | 2/1991 | Aldecoa | H01M 2/021 429/122 |
| 5,010,883 | A | 4/1991 | Rawlings et al. | |
| 5,018,515 | A | 5/1991 | Gilman | |
| 5,025,783 | A | 6/1991 | Lamb | |
| 5,028,597 | A | 7/1991 | Kodama et al. | |
| 5,037,397 | A | 8/1991 | Kalt et al. | |
| 5,086,170 | A | 2/1992 | Luheshi et al. | |
| 5,092,323 | A | 3/1992 | Riedel et al. | |
| 5,092,858 | A | 3/1992 | Benson et al. | |
| 5,100,396 | A | 3/1992 | Zamierowski | |
| 5,112,323 | A | 5/1992 | Winkler et al. | |
| 5,134,994 | A | 8/1992 | Say | |
| 5,149,331 | A | 9/1992 | Ferdman et al. | |
| 5,151,314 | A | 9/1992 | Brown | |
| 5,152,757 | A | 10/1992 | Eriksson | |
| 5,167,613 | A * | 12/1992 | Karami | A61F 13/0203 602/42 |
| 5,176,663 | A * | 1/1993 | Svedman | A61F 13/0203 128/888 |
| 5,180,375 | A * | 1/1993 | Feibus | A61F 13/36 604/264 |
| 5,215,522 | A | 6/1993 | Page et al. | |
| 5,232,453 | A | 8/1993 | Plass et al. | |

(56) References Cited

U.S. PATENT DOCUMENTS

| | | |
|---|---|---|
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A * | 10/1994 | Goldberg ............ A61B 17/3401 604/118 |
| 5,358,494 A | 10/1994 | Svedman |
| 5,384,174 A | 1/1995 | Ward et al. |
| 5,387,207 A | 2/1995 | Dyer et al. |
| 5,419,769 A * | 5/1995 | Devlin ................. A61M 1/0039 604/118 |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A * | 6/1996 | Skalla .................... A61B 18/00 604/317 |
| 5,527,293 A * | 6/1996 | Zamierowski .......... A61F 5/453 128/898 |
| 5,549,584 A * | 8/1996 | Gross .................. A61M 1/0088 604/313 |
| 5,549,585 A * | 8/1996 | Maher .................. A61M 1/0001 141/319 |
| 5,556,375 A | 9/1996 | Ewall |
| 5,585,178 A | 12/1996 | Calhoun et al. |
| 5,599,292 A * | 2/1997 | Yoon ................. A61B 17/00234 604/1 |
| 5,607,388 A | 3/1997 | Ewall |
| 5,611,373 A | 3/1997 | Ashcraft |
| 5,634,893 A * | 6/1997 | Rishton ............... A61M 1/0007 604/319 |
| 5,636,643 A * | 6/1997 | Argenta .............. A61M 1/0088 128/897 |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A * | 7/1998 | Bilbo ................. A61M 1/0023 604/317 |
| 5,807,295 A | 9/1998 | Hutcheon et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 * | 5/2003 | Stickels ................ A61F 13/023 602/41 |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 * | 11/2003 | Watson ............... A61M 1/0001 604/319 |
| 6,680,113 B1 | 1/2004 | Lucast et al. |
| 6,685,681 B2 * | 2/2004 | Lockwood .......... A61M 1/0058 502/43 |
| 6,693,180 B2 * | 2/2004 | Lee .......................... A61L 15/28 536/123.1 |
| 6,695,823 B1 * | 2/2004 | Lina .................... A61F 13/0203 602/43 |
| 6,752,794 B2 | 6/2004 | Lockwood et al. |
| 6,787,682 B2 | 9/2004 | Gilman |
| 6,814,079 B2 * | 11/2004 | Heaton ................. A61F 13/023 128/897 |
| 6,855,135 B2 * | 2/2005 | Lockwood .......... A61M 1/0058 604/313 |
| 6,856,821 B2 * | 2/2005 | Johnson ............. A61B 5/14542 600/309 |
| 6,979,324 B2 | 12/2005 | Bybordi et al. |
| 7,070,584 B2 * | 7/2006 | Johnson ............. A61M 1/0088 424/444 |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 * | 8/2002 | Johnson ............. A61B 5/14542 600/364 |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 * | 6/2003 | Solem ................ A61M 1/0088 604/540 |

(56) References Cited

U.S. PATENT DOCUMENTS

| | | | |
|---|---|---|---|
| 2003/0158577 A1* | 8/2003 | Ginn | A61B 17/0057 606/213 |
| 2003/0212357 A1* | 11/2003 | Pace | A61F 13/0203 602/41 |
| 2003/0225347 A1* | 12/2003 | Argenta | A61B 17/88 601/6 |
| 2003/0225355 A1 | 12/2003 | Butler | |
| 2004/0002676 A1 | 1/2004 | Siegwart et al. | |
| 2004/0030304 A1 | 2/2004 | Hunt et al. | |
| 2004/0064132 A1 | 4/2004 | Boehringer et al. | |
| 2004/0077984 A1 | 4/2004 | Worthley | |
| 2004/0099268 A1 | 5/2004 | Smith et al. | |
| 2004/0118401 A1 | 6/2004 | Smith et al. | |
| 2004/0127836 A1 | 7/2004 | Sigurjonsson et al. | |
| 2004/0127862 A1 | 7/2004 | Bubb et al. | |
| 2004/0133143 A1 | 7/2004 | Burton et al. | |
| 2004/0186239 A1 | 9/2004 | Qin et al. | |
| 2004/0219337 A1 | 11/2004 | Langley et al. | |
| 2004/0230179 A1* | 11/2004 | Shehada | A61B 5/0031 604/541 |
| 2005/0034731 A1 | 2/2005 | Rousseau et al. | |
| 2005/0054998 A1 | 3/2005 | Poccia et al. | |
| 2005/0059918 A1 | 3/2005 | Sigurjonsson et al. | |
| 2005/0065484 A1* | 3/2005 | Watson, Jr. | A61M 27/00 604/289 |
| 2005/0070858 A1 | 3/2005 | Lockwood et al. | |
| 2005/0101940 A1* | 5/2005 | Radl | A61M 1/0011 604/543 |
| 2005/0113732 A1 | 5/2005 | Lawry | |
| 2005/0124925 A1 | 6/2005 | Scherpenborg | |
| 2005/0131327 A1 | 6/2005 | Lockwood et al. | |
| 2005/0137539 A1 | 6/2005 | Biggie et al. | |
| 2005/0143694 A1 | 6/2005 | Schmidt et al. | |
| 2005/0159695 A1 | 7/2005 | Cullen et al. | |
| 2005/0161042 A1 | 7/2005 | Fudge et al. | |
| 2005/0163978 A1 | 7/2005 | Strobech et al. | |
| 2005/0214376 A1 | 9/2005 | Faure et al. | |
| 2005/0233072 A1 | 10/2005 | Stephan et al. | |
| 2005/0256437 A1 | 11/2005 | Silcock et al. | |
| 2005/0261642 A1 | 11/2005 | Weston | |
| 2005/0261643 A1 | 11/2005 | Bybordi et al. | |
| 2005/0277860 A1 | 12/2005 | Jensen | |
| 2006/0079852 A1 | 4/2006 | Bubb et al. | |
| 2006/0083776 A1 | 4/2006 | Bott et al. | |
| 2006/0154546 A1 | 7/2006 | Murphy et al. | |
| 2006/0236979 A1 | 10/2006 | Stolarz et al. | |
| 2006/0241542 A1 | 10/2006 | Gudnason et al. | |
| 2006/0271020 A1 | 11/2006 | Huang et al. | |
| 2007/0027414 A1 | 2/2007 | Hoffman et al. | |
| 2007/0078366 A1 | 4/2007 | Haggstrom et al. | |
| 2007/0161937 A1 | 7/2007 | Aali | |
| 2007/0185426 A1* | 8/2007 | Ambrosio | A61L 27/52 602/43 |
| 2007/0225663 A1 | 9/2007 | Watt et al. | |
| 2007/0265585 A1 | 11/2007 | Joshi et al. | |
| 2007/0265586 A1 | 11/2007 | Joshi et al. | |
| 2008/0027366 A1 | 1/2008 | Da Silva Macedo | |
| 2008/0090085 A1 | 4/2008 | Kawate et al. | |
| 2008/0119802 A1 | 5/2008 | Riesinger | |
| 2008/0138591 A1 | 6/2008 | Graham et al. | |
| 2008/0149104 A1 | 6/2008 | Eifler | |
| 2008/0173389 A1 | 7/2008 | Mehta et al. | |
| 2008/0195017 A1* | 8/2008 | Robinson | A61F 13/00068 602/44 |
| 2008/0225663 A1 | 9/2008 | Smith et al. | |
| 2008/0243044 A1 | 10/2008 | Hunt et al. | |
| 2008/0269657 A1 | 10/2008 | Brenneman et al. | |
| 2008/0271804 A1* | 11/2008 | Biggie | A61M 1/0088 138/137 |
| 2009/0025724 A1 | 1/2009 | Herron, Jr. | |
| 2009/0088719 A1 | 4/2009 | Driskell | |
| 2009/0093779 A1 | 4/2009 | Riesinger | |
| 2009/0124988 A1 | 5/2009 | Coulthard | |
| 2009/0177172 A1 | 7/2009 | Wilkes | |
| 2009/0216204 A1 | 8/2009 | Bhavaraju et al. | |
| 2009/0227969 A1 | 9/2009 | Jaeb et al. | |
| 2009/0264807 A1 | 10/2009 | Haggstrom et al. | |
| 2009/0292264 A1 | 11/2009 | Hudspeth et al. | |
| 2009/0312662 A1 | 12/2009 | Colman et al. | |
| 2009/0326487 A1 | 12/2009 | Vitaris | |
| 2009/0326488 A1 | 12/2009 | Budig et al. | |
| 2010/0028390 A1 | 2/2010 | Cleary et al. | |
| 2010/0063467 A1 | 3/2010 | Addison et al. | |
| 2010/0106106 A1 | 4/2010 | Heaton et al. | |
| 2010/0106118 A1 | 4/2010 | Heaton et al. | |
| 2010/0125259 A1 | 5/2010 | Olson | |
| 2010/0159192 A1 | 6/2010 | Cotton | |
| 2010/0185163 A1 | 7/2010 | Heagle | |
| 2010/0226824 A1 | 9/2010 | Ophir et al. | |
| 2010/0262090 A1 | 10/2010 | Riesinger | |
| 2010/0267302 A1 | 10/2010 | Kantner et al. | |
| 2010/0305490 A1 | 12/2010 | Coulthard et al. | |
| 2010/0305524 A1 | 12/2010 | Vess et al. | |
| 2010/0318072 A1 | 12/2010 | Johnston et al. | |
| 2010/0324510 A1* | 12/2010 | Andresen | A61M 1/0088 604/319 |
| 2010/0324516 A1 | 12/2010 | Braga et al. | |
| 2011/0046585 A1 | 2/2011 | Weston | |
| 2011/0137271 A1 | 6/2011 | Andresen et al. | |
| 2011/0160686 A1 | 6/2011 | Ueda et al. | |
| 2011/0171480 A1 | 7/2011 | Mori et al. | |
| 2011/0172617 A1 | 7/2011 | Riesinger | |
| 2011/0224631 A1 | 9/2011 | Simmons et al. | |
| 2011/0229688 A1 | 9/2011 | Cotton | |
| 2011/0244010 A1 | 10/2011 | Doshi | |
| 2011/0257617 A1 | 10/2011 | Franklin | |
| 2012/0016322 A1 | 1/2012 | Coulthard et al. | |
| 2012/0019031 A1 | 1/2012 | Bessert | |
| 2012/0040131 A1 | 2/2012 | Speer | |
| 2012/0123359 A1 | 5/2012 | Reed | |
| 2012/0143157 A1 | 6/2012 | Riesinger | |
| 2012/0258271 A1 | 10/2012 | Maughan | |
| 2013/0030394 A1 | 1/2013 | Locke et al. | |
| 2013/0053746 A1 | 2/2013 | Roland et al. | |
| 2013/0066285 A1 | 3/2013 | Locke et al. | |
| 2013/0096518 A1 | 4/2013 | Hall et al. | |
| 2013/0152945 A1 | 6/2013 | Locke et al. | |
| 2014/0039423 A1 | 2/2014 | Riesinger | |
| 2014/0039424 A1 | 2/2014 | Locke | |
| 2014/0141197 A1 | 5/2014 | Hill et al. | |
| 2014/0155849 A1 | 6/2014 | Heaton et al. | |
| 2014/0163491 A1 | 6/2014 | Schuessler et al. | |
| 2014/0171851 A1 | 6/2014 | Addison | |
| 2014/0309574 A1 | 10/2014 | Cotton | |
| 2014/0350494 A1 | 11/2014 | Hartwell et al. | |
| 2014/0352073 A1 | 12/2014 | Goenka | |
| 2015/0030848 A1 | 1/2015 | Goubard | |
| 2015/0080788 A1 | 3/2015 | Blott et al. | |
| 2015/0119830 A1 | 4/2015 | Luckemeyer et al. | |
| 2015/0119833 A1 | 4/2015 | Coulthard et al. | |
| 2015/0190286 A1 | 7/2015 | Allen et al. | |
| 2016/0000610 A1 | 1/2016 | Riesinger | |
| 2016/0067107 A1 | 3/2016 | Cotton | |
| 2016/0144084 A1 | 5/2016 | Collinson et al. | |

FOREIGN PATENT DOCUMENTS

| | | |
|---|---|---|
| AU | 755496 | 2/2002 |
| AU | 2009200608 A1 | 10/2009 |
| CA | 2005436 | 6/1990 |
| CN | 87101823 A | 8/1988 |
| DE | 26 40 413 A1 | 3/1978 |
| DE | 43 06 478 A1 | 9/1994 |
| DE | 295 04 378 U1 | 10/1995 |
| DE | 202004018245 U1 | 7/2005 |
| DE | 202014100383 U1 | 2/2015 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |

(56) References Cited

FOREIGN PATENT DOCUMENTS

| | | | |
|---|---|---|---|
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 B1 | 8/2004 |
| EP | 2578193 A1 | 4/2013 |
| GB | 692578 | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 4129536 | 4/1992 |
| JP | 2005205120 A | 8/2005 |
| JP | 2007254515 A | 10/2007 |
| JP | 2008080137 A | 4/2008 |
| SG | 71559 | 3/1999 |
| WO | 80/02182 A1 | 10/1980 |
| WO | 87/04626 A1 | 8/1987 |
| WO | 8707164 A1 | 12/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2008149107 A1 | 12/2008 |
| WO | 2009002260 A1 | 12/2008 |
| WO | WO 2009002260 A1 * | 12/2008 | ......... A61M 1/0088 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010016791 A1 | 2/2010 |
| WO | 2010032728 A1 | 3/2010 |
| WO | 01/36188 A2 | 5/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

International Search Report and Written Opinion dated Jun. 1, 2011 for PCT International Application No. PCT/US2011/028344.
International Search Report and Written Opinion for PCT/US2014/056508 dated Dec. 9, 2014.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.

(56) References Cited

OTHER PUBLICATIONS

Non-Final Office Action dated Jul. 20, 2011 for U.S. Appl. No. 12/398,904.
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2011.
Response filed Oct. 21, 2011 for U.S. Appl. No. 12/398,891.
Interview Summary dated Oct. 27, 2011 for U.S. Appl. No. 12/398,891.
Restriction Requirement date dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written US2009/036217 Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, dated Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 dated Sep. 30, 2015.
International Search Report and Written Opinion for PCT/US2015/029037 dated Sep. 4, 2015.
International Search Report and Written Opinion for PCT/U52015/034289 dated Aug. 21, 2015.
International Search Report and Written Opinion for PCT/U52015/065135 dated Apr. 4, 2016.
International Search Report and Written Opinion for PCT/GB2012/050822 dated Aug. 8, 2012.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for EP 11714148.1, dated May 2, 2014.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain—Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
European Search Report for corresponding EP Application 171572787 dated Jun. 6, 2017.
International Search Report and Written Opinion for corresponding application PCT/US2016/031397.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Office Action for related U.S. Appl. No. 14/965,675, dated Jan. 31, 2018.
International Search Report and Written Opinion for related application PCT/US2016/047351, dated Nov. 2, 2016.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for PCT/US2017/058209, dated Jan. 10, 2018.
Extended European Search Report for related application 17177013.4, dated Mar. 19, 2018.
Extended European Search Report for related application 16793298.7, dated Mar. 27, 2018.
Office Action for related U.S. Appl. No. 15/307,472, dated Oct. 18, 2018.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 15/265,718, dated Feb. 7, 2019.

\* cited by examiner

DELIVERY-AND-FLUID-STORAGE BRIDGES FOR USE WITH REDUCED-PRESSURE SYSTEMS

RELATED APPLICATION

This application is a continuation application of U.S. patent application Ser. No. 13/046,164, entitled "Delivery-and-Fluid-Storage Bridges For Use With Reduced-Pressure Systems," filed Mar. 11, 2011, which claims the benefit, under 35 USC § 119(e), of the filing of U.S. Provisional Patent Application Ser. No. 61/314,299, entitled "Delivery-and-Fluid-Storage Bridges For Use With Reduced-Pressure Systems," filed Mar. 16, 2010, each of which are incorporated herein by reference for all purposes.

BACKGROUND

The present disclosure relates generally to medical treatment systems and, more particularly, but not by way of limitation, to delivery-and-fluid-storage bridges and pumps for use with or as an aspect of reduced-pressure treatment systems.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad distributes reduced pressure to the tissue and channels fluids that are drawn from the tissue.

SUMMARY

According to an illustrative embodiment, a reduced-pressure treatment system for applying reduced pressure to a tissue site on a patient includes a reduced-pressure source for supplying reduced pressure, a treatment manifold for placing proximate the tissue site and adapted to distribute reduced pressure to the tissue site, a sealing member for placing over the tissue site and adapted to form a fluid seal over the tissue site and treatment manifold. The sealing member has a treatment aperture. The system further includes a delivery-and-fluid-storage bridge having a first longitudinal end and a second longitudinal end and a first side and a second, patient-facing side. The delivery-and-fluid-storage bridge includes a delivery manifold extending along a length of the delivery-and-fluid-storage bridge for delivering reduced pressure to the treatment manifold, an absorbent layer proximate the delivery manifold is adapted to receive and absorb fluids. The delivery manifold is formed from a first material and the absorbent layer is formed from a second material. The first material and second material differ in properties. The delivery-and-fluid-storage bridge further includes a first encapsulating layer and a second encapsulating layer at least partially enclosing the delivery manifold and absorbent layer. A first aperture is formed on the first side of the delivery-and-fluid-storage bridge proximate the first longitudinal end. The first aperture is fluidly coupled to the reduced-pressure source. A second aperture is formed on the second side of the delivery-and-fluid-storage bridge proximate the second longitudinal end. The second aperture is fluidly coupled to the treatment manifold over the treatment aperture in the sealing member. Reduced pressure is transferred from the first aperture along the distribution manifold to the second aperture and to the tissue site.

According to another illustrative, a delivery-and-fluid-storage bridge for use with a reduced-pressure treatment system includes a delivery manifold extending along a length of the delivery-and-fluid-storage bridge for delivering reduced pressure to a tissue site, an absorbent layer proximate the delivery manifold adapted to receive and absorb fluids, and wherein the delivery-and-fluid-storage bridge has a first side and a second, patient-facing side. The delivery-and-fluid-storage bridge further includes a first encapsulating layer and a second encapsulating layer at least partially enclosing the delivery manifold and absorbent layer. A first aperture is formed proximate the first longitudinal end of the delivery-and-fluid-storage bridge on the first side for fluidly communicating reduced pressure to the delivery manifold from a reduced-pressure source. A second aperture is formed on the second, patient-facing side of the second encapsulating layer for transmitting reduced pressure to a tissue site.

According to another illustrative embodiment, a delivery-and-fluid-storage bridge for use with a reduced-pressure treatment system includes a plurality of delivery manifolds extending along a length of the delivery-and-fluid-storage bridge for delivering reduced pressure to a tissue site, an absorbent layer proximate the plurality of delivery manifolds adapted to receive and absorb fluids, and an encapsulating pouch encapsulating the plurality of delivery manifolds and the absorbent layer. The encapsulating pouch includes a first encapsulating layer and a second encapsulating layer at least partially enclosing the delivery manifold and absorbent layer. The second encapsulating layer defines the second, patient-facing side of the delivery-and-fluid-storage bridge. A first aperture is formed proximate the first longitudinal end of the delivery-and-fluid-storage bridge for fluidly communicating reduced pressure to the delivery manifold from a reduced-pressure source. A second aperture is formed on the patient-facing side of the first encapsulating layer for transmitting reduced pressure to a tissue site.

According to another illustrative embodiment, a method for treating a tissue site utilizing a delivery-and-fluid-storage bridge includes placing a treatment manifold proximate the tissue site and providing a delivery-and-fluid-storage bridge. The delivery-and-fluid-storage bridge includes a delivery manifold extending along a length of the delivery-and-fluid-storage bridge for delivering reduced pressure to a tissue site, an absorbent layer proximate the delivery manifold adapted to receive and absorb fluids, and an encapsulating pouch encapsulating the delivery manifold and the absorbent layer. The encapsulating pouch includes a first encapsulating layer and a second encapsulating layer at least partially enclosing the delivery manifold and absorbent layer. The second encapsulating layer defines the second, patient-facing side of the delivery-and-fluid-storage bridge. A first aperture is formed on the delivery-and-fluid-storage bridge proximate the first longitudinal end for fluidly communicating reduced pressure to the delivery manifold from a reduced-pressure source, and a second aperture is formed on the patient-facing side of the second encapsulating layer for transmitting reduced pressure to a tissue site. The method further includes placing the second longitudinal end of the delivery-and-fluid-storage bridge proximate the treatment manifold, applying a reduced pressure to the first longitudinal end of the delivery-and-fluid-storage bridge through the first aperture, and communicating the reduced pressure along the reduced-pressure bridge through the delivery manifold to a second longitudinal end of the reduced-pressure bridge. The method also includes applying the reduced pressure through the second aperture to the treatment manifold proximate the tissue site, receiving fluids through the second aperture from the tissue site, and wicking fluids extracted from the tissue site through the second longitudinal end into the absorption layer positioned proximate the delivery manifold.

According to another illustrative embodiment, a method of manufacturing a delivery-and-fluid-storage bridge includes providing a delivery manifold, placing an absorbent layer proximate the delivery manifold, and encapsulating the delivery manifold and absorbent layer in an encapsulated pouch. The encapsulating pouch includes a first encapsulating layer and a second encapsulating layer at least partially enclosing the delivery manifold and absorbent layer. The second encapsulating layer defines the second, patient-facing side of the delivery-and-fluid-storage bridge. The method also includes forming a first aperture is formed proximate the first longitudinal end of the delivery-and-fluid-storage bridge for fluidly communicating reduced pressure to the delivery manifold from a reduced-pressure source. The method further includes forming a second aperture on the patient-facing side of the second encapsulating layer for transmitting reduced pressure to a tissue site.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
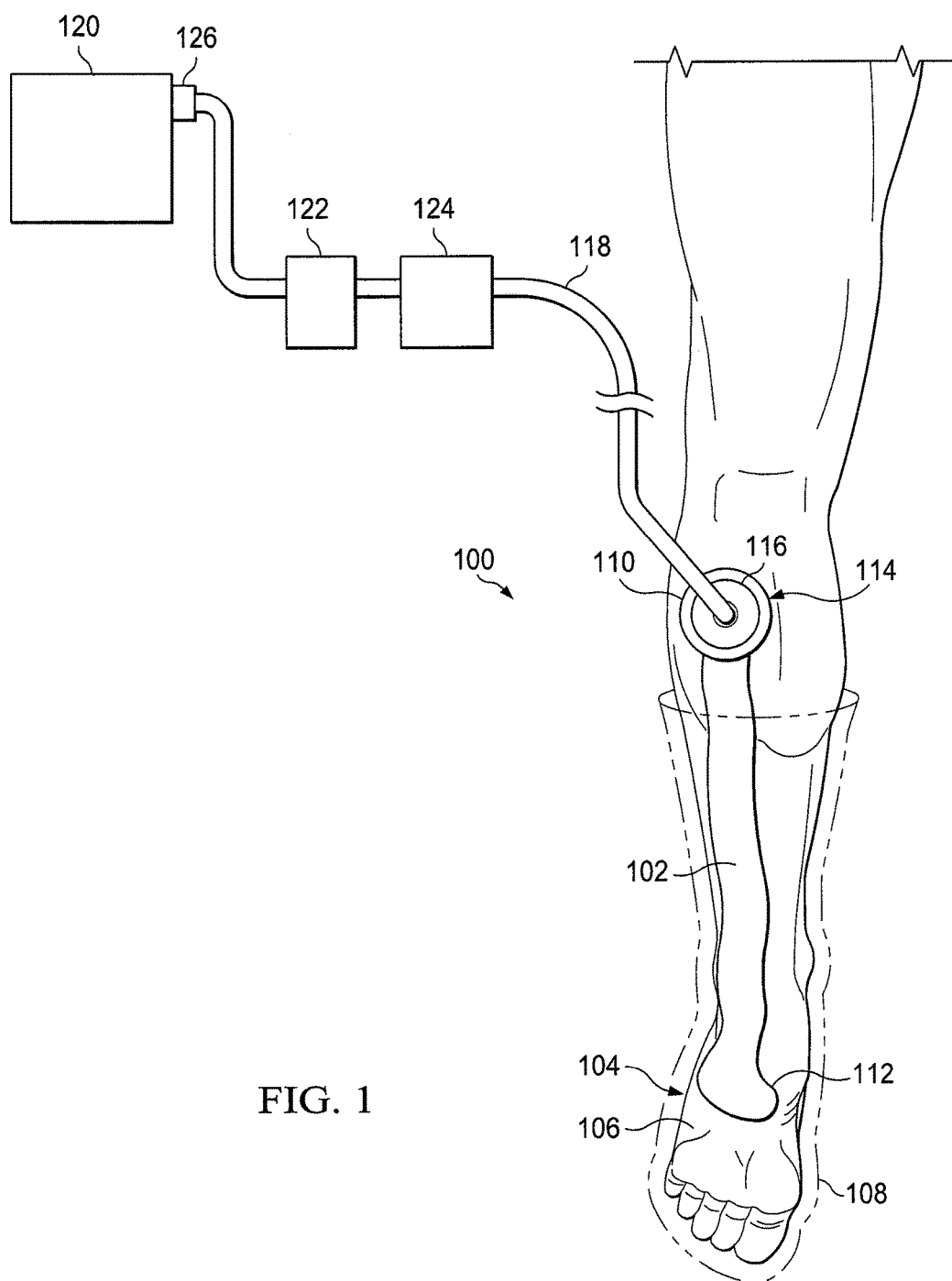
FIG. 1 is a schematic, perspective view with a portion shown as a block diagram of an illustrative reduced-pressure treatment system utilizing a delivery-and-fluid-storage bridge.

Referring primarily to FIG. 1, an illustrative embodiment of a reduced-pressure treatment system 100 is presented. The reduced-pressure treatment system 100 includes an illustrative embodiment of a delivery-and-fluid-storage bridge 102. The delivery-and-fluid-storage bridge 102 facilitates reduced-pressure treatment of a tissue site 104 and is particularly useful in treating a limited-access tissue site, which in this illustration is on the bottom sole (plantar) of a patient's foot 106 and also within an offloading device, e.g., offloading boot 108 (shown in hidden lines). A treatment manifold 109 (see FIG. 3) may be located at the tissue site 104.

The reduced-pressure treatment system 100 may be used with a tissue site at a non-limited-access site or a limited-access site. Other illustrative examples of limited-access tissue sites include on a patient's back, under a compression garment, in a total contact casting (TCC), in a removable walker, in a healing sandal, in a half shoe, or in an ankle foot orthoses. The reduced-pressure treatment system 100 may be used with the bodily tissue of any human, animal, or other organism, including bone tissue, adipose tissue, muscle tissue, dermal tissue, vascular tissue, connective tissue, cartilage, tendons, ligaments, or any other tissue.

The delivery-and-fluid-storage bridge 102 provides a low profile source of reduced pressure to be supplied to the tissue site 104 and thereby may increase patient comfort and enhance reliability of the reduced-pressure supply to the tissue site 104. Because of the low profile of the delivery-and-fluid-storage bridge 102, the delivery-and-fluid-storage bridge 102 may readily be used with an offloading device. The low profile of the delivery-and-fluid-storage bridge 102 allows the delivery-and-fluid-storage bridge 102 to be used in numerous situations without raising pressure at a particular location, which can lead to the formation of pressure ulcers. The delivery-and-fluid-storage bridge 102 may allow the patient the benefit of both reduced-pressure treatment as well as the offloading of physical pressure.

Figure 2:
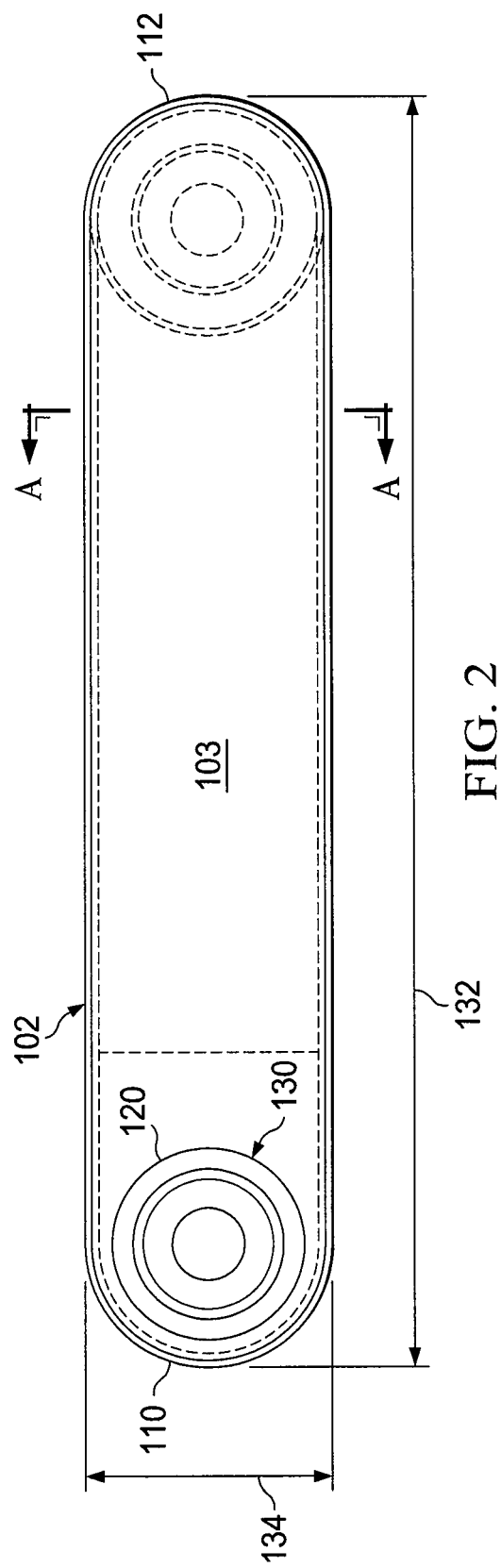
FIG. 2 is a schematic, plan view of the delivery-and-fluid-storage bridge of FIG. 1 shown with another illustrative reduced-pressure source.
Figure 3:
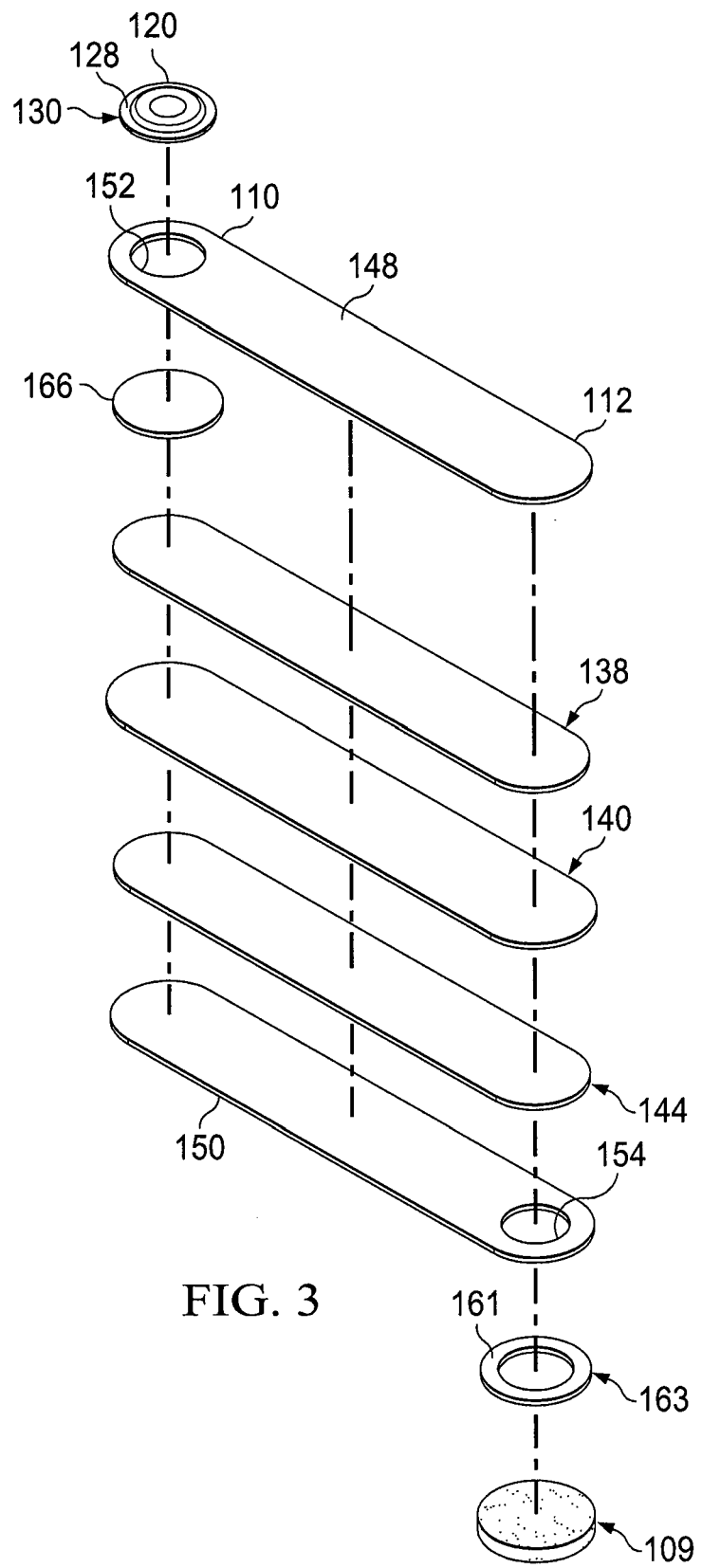
FIG. 3 is a schematic, exploded, perspective view of the delivery-and-fluid-storage bridge of FIG. 1 and further including a treatment manifold.

With reference to FIGS. 1-3, the delivery-and-fluid-storage bridge 102 has a first longitudinal end 110 and a second longitudinal end 112. The second longitudinal end 112 is placed proximate the limited-access tissue site 104. The first longitudinal end 110 has a reduced-pressure-interface site 114 that is for receiving a reduced-pressure interface 116, which may be an aperture or port connector, such as a TRAC Pad® interface or a SensaT.R.A.C.™ pad interface from Kinetic Concepts, Inc. of San Antonio, Tex. A first aperture 152 (see FIG. 3) is formed on a first side 103 of the delivery-and-fluid-storage bridge 102 to allow the reduced-pressure interface 116 to fluidly communicate with an interior of the delivery-and-fluid-storage bridge 102.

The first longitudinal end 110 is typically placed at a location on or near the patient that provides convenient access by the healthcare provider, such as a convenient location for applying reduced-pressure to the reduced-pressure-interface site 114. If a reduced-pressure interface 116 is attached at the first longitudinal end 110 at the first aperture 152, any type of reduced-pressure source may be attached to the reduced-pressure interface 116. For example, a pump could be attached to the reduced-pressure interface 116 or a reduced-pressure delivery conduit 118 could be attached with a remote reduced-pressure source. When an offloading device, e.g., offloading boot 108, is utilized, the delivery-and-fluid-storage bridge 102 would extend from the tissue site 104 to a place outside of the offloading device. The actual longitudinal length (L) 132 (see FIG. 2) of the delivery-and-fluid-storage bridge 102 may be varied to support use with a particular offloading device or application.

A reduced-pressure delivery conduit 118 may fluidly couple the reduced-pressure interface 116 to a reduced-pressure source 120 or the reduced-pressure source 120 may be formed integrally with the delivery-and-fluid-storage bridge 102 as discussed further below. The reduced-pressure source 120 may be any device for supplying a reduced pressure, such as a vacuum pump, wall suction, or integrated micro-pump. While the amount and nature of reduced pressure applied to a tissue site will typically vary according to the application, the reduced pressure will typically be between −5 mm Hg (−667 Pa) and −500 mm Hg (−66.7 kPa) and more typically between −25 mm Hg (−3.33 kPa) and −200 mm Hg (−26.6 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure. For vertical applications of the delivery-and-fluid-storage bridge 102, such as is shown in FIG. 1 on an ambulatory patient's leg, a specified minimum reduced pressure may be necessary to ensure proper fluid flow. For example in one embodiment, a reduced pressure of at least −125 mm Hg (−16.66 kPa) has been suggested as a minimum, but other pressures may be suitable for different situations.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. In one illustrative embodiment, a V.A.C.® Therapy Unit by Kinetic Concepts, Inc. of San Antonio may be used as the reduced-pressure source 120.

If the reduced-pressure interface 116 is attached at the first longitudinal end 110 at the first aperture 152, any type of reduced-pressure source 120 may be attached to the reduced-pressure interface 116. For example, a pump, such as micro-pump 128, could be attached to the reduced-pressure interface 116 or a reduced-pressure delivery conduit 118 could be attached with a remote reduced-pressure source.

Depending on the application, a plurality of devices may be fluidly coupled to the reduced-pressure delivery conduit 118. For example, a fluid canister 122 or a representative device 124 may be included. The representative device 124 may be another fluid reservoir or canister to hold exudates and other fluids removed. Other examples of the representative device 124 that may be included on the reduced-pressure delivery conduit 118 include the following non-limiting examples: a pressure-feedback device, a volume detection system, a blood detection system, an infection detection system, a flow monitoring system, a temperature monitoring system, a filter, etc. Some of these devices may be formed integrally with the reduced-pressure source 120. For example, a reduced-pressure port 126 on the reduced-pressure source 120 may include a filter member that includes one or more filters, e.g., an odor filter.

Figure 4:
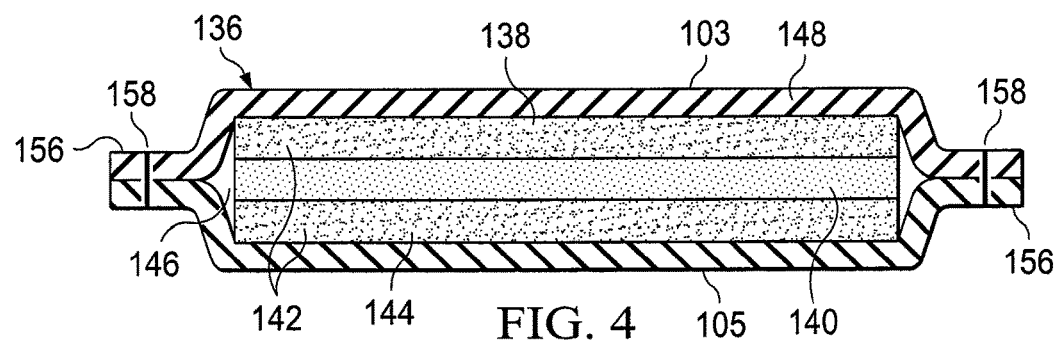
FIG. 4 is a schematic, cross-sectional view of the of the delivery-and-fluid-storage bridge of FIGS. 1-3 taken along line A-A in FIG. 2.

Referring now primarily to FIGS. 2-5, the delivery-and-fluid-storage bridge 102 of FIG. 1 is described with additional details and with a different reduced-pressure source 120. The delivery-and-fluid-storage bridge 102 has the first side 103 and a second, patient-facing side 105. FIGS. 2-4 are shown with an alternative arrangement for the reduced-pressure source 120, which is shown as a micro-pump 128, such as a piezoelectric pump 130 or manually-actuated pump. As shown clearly in FIG. 2, the delivery-and-fluid-storage bridge 102 has a longitudinal length 132 and a width 134.

Figure 5:
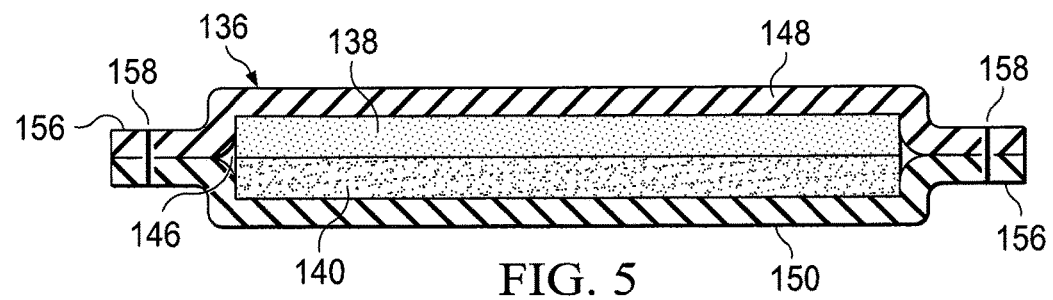
FIG. 5 is a schematic, cross-sectional view of an illustrative embodiment of a delivery-and-fluid-storage bridge.

The delivery-and-fluid-storage bridge 102 has an encapsulating pouch 136 that encapsulates fully or partially at least a first delivery manifold 138 and at least one absorbent layer 140 as shown in FIG. 5 or a plurality of delivery manifolds 142 and at least one absorbent layer 140 as shown in FIG. 4. The plurality of delivery manifolds 142 is presented in FIG. 4 as the first delivery manifold 138 and a second delivery manifold 144. The delivery manifolds 138, 142, 144 typically run the longitudinal length 132 of the delivery-and-fluid-storage bridge 102 in an interior portion 146. The delivery manifolds 138, 142, 144 operate to deliver reduced pressure from the first longitudinal end 110 to the second longitudinal end 112 of the delivery-and-fluid-storage bridge 102. The absorbent layer 140 receives and absorbs fluids. The absorbent layer 140 typically pulls fluids, e.g., exudate, from the delivery manifolds 138, 142, 144 and stores the fluids.

The delivery manifolds 138, 142, 144 and the treatment manifold 109 may be formed from any manifold material for distributing reduced pressure. The term "manifold" as used herein generally refers to a substance or structure that is provided to assist in applying reduced pressure to, delivering fluids to, or removing fluids from a location, such as a tissue site. The manifold material typically includes a plurality of flow channels or pathways that distribute fluids provided to and removed from locations around the manifold material. In one illustrative embodiment, the flow channels or pathways are interconnected to improve distribution of fluids. Examples of manifold materials may include, without limitation, devices that have structural elements arranged to form flow channels, such as, for example, cellular foam, open-cell foam, porous tissue collections, liquids, gels, non-wovens, and foams that include, or cure to include, flow channels. The manifold material may be porous and may be made from foam, gauze, felted mat, or any other material suited to transport fluids. In one embodiment, the manifold material is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include "closed cells" at least on portions.

The delivery manifolds 138, 142, 144 may be formed from a manifold material that may be a high-wicking manifold material, such as a capillary material or non-woven material. The high-wicking material used for the delivery manifold material may allow the delivery-and-fluid-storage bridge 102 to operate removing the fluid through the delivery-and-fluid-storage bridge 102 even without reduced pressure being applied.

The absorbent layer 140 may be formed from any material that is adapted to receive and store fluids. For example, without limitation, the absorbent layer 140 may be formed from one or more of the following: capillary-containing material, super absorbent fiber/particulates, hydrofiber, sodium carboxymethyl cellulose, alginates, sodium polyacrylate, or other suitable material. The absorbent layer 140 and the manifold material used for the delivery manifolds 138, 142, 144 may in some illustrative embodiments be treated with a plasma coating to increase the hydrophilic properties and to thereby aid in fluid transfer through the system. The hydrophilic properties of the manifolds 138, 142, 144 may also be enhanced by coating the manifolds 138, 142, 144 with a dip or spray of a suitable material such as a HYDAK coating. Use of the absorbent layer 140 as an aspect of the reduced-pressure treatment system 100 allows the fluids removed to be stored locally, i.e., fairly close to the tissue site 104, such that the removed fluids are not transported a great distance.

The encapsulating pouch 136 typically is formed with a first encapsulating layer 148 and a second encapsulating layer 150 that at least partially enclose the delivery manifold(s) 138, 142, 144 and absorbent layer 140. The second encapsulating layer 150 is the second, patient-facing side 105 of the delivery-and-fluid-storage bridge 102. The first aperture 152 is formed proximate the first longitudinal end 110 of the delivery-and-fluid-storage bridge 102 on the first encapsulating layer 148. The first aperture 152 is for fluidly communicating reduced pressure to the delivery manifold(s) 138, 142, 144 from the reduced-pressure source 120. A second aperture 154 is formed on the second, patient-facing side 105 of the second encapsulating layer 150 for transmitting reduced pressure from the interior portion 146 to the tissue site 104. An anti-microbial additive may be included in the interior portion 146 to help control bacteria growth.

The first encapsulating layer 148 and the second encapsulating layer 150 have peripheral edges 156 that may be coupled to form the encapsulating pouch 136. The peripheral edges 156 may be coupled using any technique. As used herein, the term "coupled" includes coupling via a separate object and includes direct coupling. The term "coupled" also encompasses two or more components that are continuous with one another by virtue of each of the components being formed from the same piece of material. The term "coupled" may include chemical, such as via a chemical bond, adhesive, mechanical, or thermal coupling. Coupling may include without limitation welding (e.g., ultrasonic or RF welding), bonding, adhesives, cements, etc. Fluid coupling means that fluid is in communication between the designated parts or locations. Thus, the first encapsulating layer 148 and the second encapsulating layer 150 may be coupled among other ways by weld 158.

The encapsulating layers 148, 150 may be formed from any material that provides a fluid seal about the interior portion 146 that allows a reduced-pressure to be maintained therein for a given reduced-pressure source. The encapsulating layers 148, 150 may, for example, be an impermeable or semi-permeable, elastomeric material. For semi-permeable materials, the permeability must be low enough that for a given reduced-pressure source, the desired reduced pressure may be maintained. "Elastomeric" means having the properties of an elastomer. Elastomeric material generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

Figure 6:
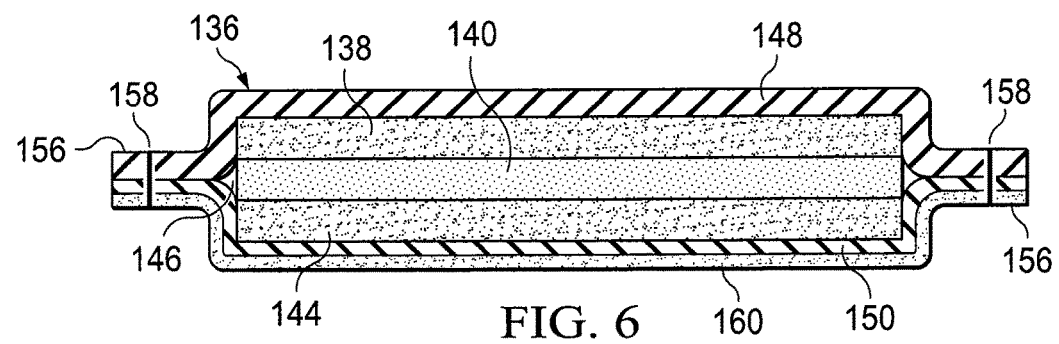
FIG. 6 is a schematic, cross-sectional view of an illustrative embodiment of a delivery-and-fluid-storage bridge.

As shown in FIG. 6, a moisture removing device 160, e.g., a wicking layer, may be coupled to an exterior portion of the second encapsulating layer 150 to provide comfort and remove fluids from against a patient's skin. The moisture removing device 160 may be a cloth-material drape, a non-woven fabric, a knitted polyester woven textile material, such as the one sold under the name InterDry® AG material from Coloplast A/S of Denmark, GORTEX® material, DuPont Softesse® material, etc.

An adhesive member or members 161, e.g., adhesive ring 163, may be applied to the second, patient-facing side 105 of the delivery-and-fluid-storage bridge 102 proximate the second aperture 154. The adhesive member(s) 161 helps form a fluid seal proximate the tissue site 104—either on a sealing member (see, e.g., 315 in FIG. 10) or directly over the tissue site and a portion of the patient's skin.

Figure 7:
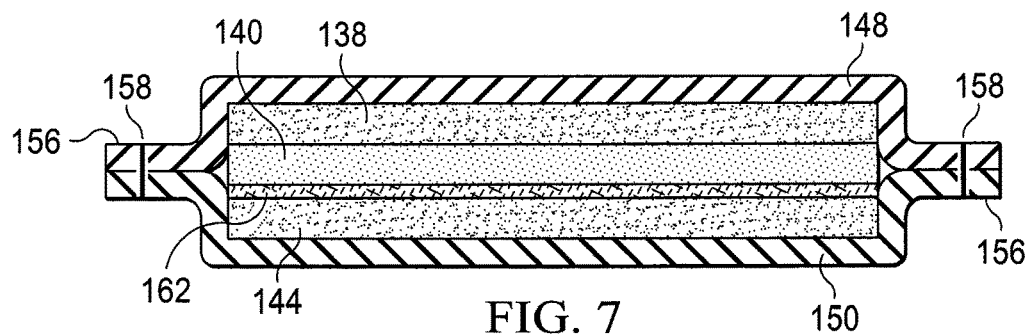
FIG. 7 is a schematic, cross-sectional view of an illustrative embodiment of a delivery-and-fluid-storage bridge.
Figure 8:
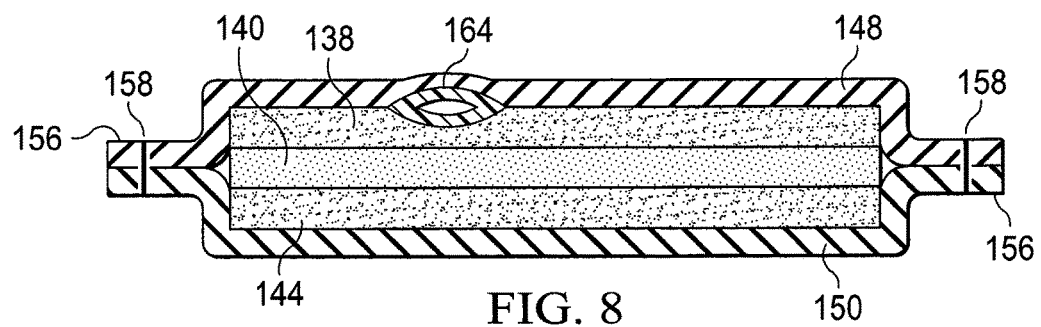
FIG. 8 is a schematic, cross-sectional view of an illustrative embodiment of a delivery-and-fluid-storage bridge.

Additional items may disposed in the interior portion 146 at discrete locations or along the longitudinal length 132 of the delivery-and-fluid-storage bridge 102. For example, as shown in FIG. 7, an odor-controlling device 162 may be disposed within the interior portion 146. The odor-controlling device 162 may be, for example, a charcoal filter. An anti-microbial additive may be included in the interior portion 146 to help control bacteria growth. As another example, as shown in FIG. 8, a single-lumen or multi-lumen conduit 164 may be disposed within the interior portion 146. The conduit 164 may facilitate measurement of the pressure at the tissue site or proximate the tissue site. The conduit 164 could either terminate proximate the first longitudinal end 110 of the delivery-and-fluid-storage bridge 102 or could continue the longitudinal length 132 of the delivery-and-fluid-storage bridge 102 to the second longitudinal end 112. A hydrophobic filter 166 may be included proximate the first aperture 152 to prevent fluids, e.g., exudate or other fluids, from exiting the delivery-and-fluid-storage bridge 102.

A color change dye may be included at the first longitudinal end 110 of the delivery-and-fluid-storage bridge 102 in order to provide feedback on the status of the absorbent layer 140. The color change dye may change colors or tone when the color change dye becomes wet thereby providing a visual indication that the delivery-and-fluid-storage bridge 102 is full. Moreover, color change dye may be positioned at various locations or continually along the delivery-and-fluid-storage bridge 102 to provide a progressive indications of capacity used, e.g., 25%, 50%, 75%, 100% used. Electrodes in the delivery-and-fluid-storage bridge 102 may be included at the first longitudinal end to form a galvanic cell that provides a voltage when the electrodes are covered by exudate or other removed liquids. In addition, the lumen 164 could monitor pressure at the second longitudinal end 112 and this information could be compared with pressure at the reduced-pressure source 120 to determine the pressure drop across the system 100 and thereby the saturation determined.

In another embodiment, the lumen 164 may be formed using a portion of the first encapsulating layer 148 or second encapsulating layer 150 and an additional longitudinal sheet secured to an inward-facing surface of the first encapsulating layer 148 or second encapsulating layer 150 to form the lumen 164. In still another embodiment, the lumen 164 may have a manifolding material disposed within the lumen 164. In still another embodiment, a longitudinal manifold material may be placed between the first encapsulating layer 148 and second encapsulating layer 150 near a periphery where the first encapsulating layer 148 and second encapsulating layer 150 otherwise directly touch. A seal or bond may be formed on each side of the longitudinal manifold material to form the lumen 164 with the manifold material therein.

In operation, the treatment manifold 109 may be placed into or proximate the tissue site 104. A sealing member (see, e.g., sealing member 315 in FIG. 10) may be placed over the treatment manifold 109 and a portion of the patient's skin. The adhesive member 161 may be used to seal the second longitudinal end 112 of the delivery-and-fluid-storage bridge 102 to the patient over the tissue site 104. The adhesive member 161 helps form a fluid seal between the delivery-and-fluid-storage bridge 102 and either the sealing member or the patient's skin. "Fluid seal," or "seal," means a seal adequate to maintain reduced pressure at a desired site given the particular reduced-pressure source or subsystem involved.

The longitudinal length 132 of the delivery-and-fluid-storage bridge 102 may be used to position the first longitudinal end 110 at a convenient location to either attach the reduced-pressure interface 116 and reduced-pressure delivery conduit 118 as shown in FIG. 1 or to conveniently access a micro-pump 128 as shown in FIG. 3. An adhesive tape or wrap may be used to hold the delivery-and-fluid-storage bridge 102 against a portion of the patient's body. Once deployed, the reduced-pressure source 120 is activated.

As the reduced-pressure source 120 is activated, the reduced-pressure source 120 communicates the reduced pressure along the delivery-and-fluid-storage bridge 102 through the delivery manifold(s) 138, 142, 144 to the second longitudinal end 112 of the delivery-and-fluid-storage bridge 102. The reduced pressure is then applied through the second aperture 154 to the treatment manifold 109 proximate the tissue site 104. In addition, typically, fluids are extracted from the tissue site 104 and received through the second aperture 154. After entering the interior portion 146, the fluids are recruited into the absorbent layer 140 positioned proximate the delivery manifold(s) 138, 142, 144. The fluids are substantially recruited and maintained in the absorbent layer 140. As a result, typically reduced pressure may be transported relatively more efficiently through the delivery manifold(s) 138, 142, 144. In this way, the reduced pressure need not overcome gravity's influence on a column of liquid to the same degree as the reduced pressure otherwise would. Typically, the pressure drop realized over the delivery-and-fluid-storage bridge 102 is constant until the absorbent layer 140 becomes saturated. As previously noted, a high-wicking material may be used for the delivery manifold material in order to allow the delivery-and-fluid-storage bridge 102 to remove the fluid through the delivery-and-fluid-storage bridge 102 even without reduced pressure being applied.

Thus, the delivery-and-fluid-storage bridge 102 may be particularly useful in avoiding a situation in which excessive fluid from a tissue site is held against gravity by reduced pressure alone. The delivery-and-fluid-storage bridge 102 moves liquids into storage and provides a flow path for gases. The liquids are drawn into the absorbent layer 140 and the gases are allowed to remain in the delivery manifolds 138, 142, 144. By using this approach, the reduced-pressure source 120 does not have to be modulated as the amount of fluid in the delivery-and-fluid-storage bridge 102 increases. Typically, the pressure drop realized over the delivery-and-fluid-storage bridge 102 is constant until the absorbent layer 140 becomes saturated.

Figure 9:
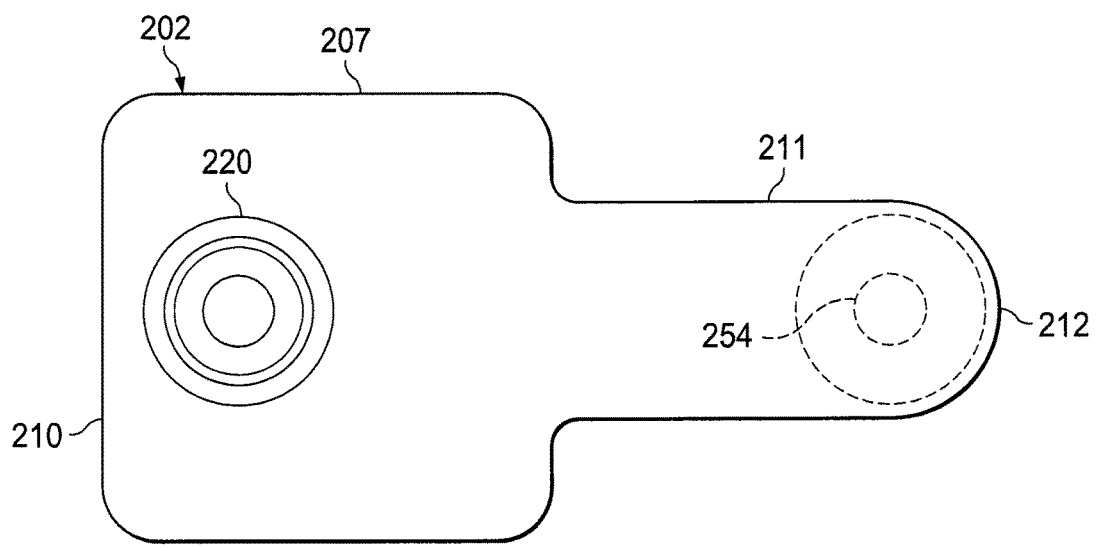
FIG. 9 is a schematic, plan view of another illustrative embodiment of a delivery-and-fluid-storage bridge.

Referring now primarily to FIG. 9, another illustrative, non-limiting embodiment of a delivery-and-fluid-storage bridge 202 is presented. In most respects, the delivery-and-fluid-storage bridge 202 is analogous to the delivery-and-fluid-storage bridge 102 of FIGS. 1-4 and like or corresponding reference numerals have been indexed by 100. The delivery-and-fluid-storage bridge 202 has a first longitudinal end 210 and a second longitudinal end 212. The first longitudinal end 210 includes a reduced-pressure source 220. The second longitudinal end includes an aperture 254 for communicating reduced pressure on the patient-facing side of the delivery-and-fluid-storage bridge 202.

The delivery-and-fluid-storage bridge 202 further includes a reservoir portion 207 and a placement portion 211. The reservoir portion 207 has a first aspect ratio (length/width) $AR_1$ and the placement portion 211 has a second aspect ratio $AR_2$. The placement portion has a higher aspect ration to facilitate placement of the second longitudinal end 212 and the reservoir portion 207 has a lower aspect ratio ($AR_2 > AR_1$). Stated in other terms, the area ($A_1$) in plan view of the reservoir portion 207 is greater than the area ($A_2$) in plan view of the placement portion 211, i.e., $A_1 > A_2$. The placement portion 211 facilitates easy placement and positioning of the second longitudinal end 212 in limited-access tissue sites and the reservoir portion 207 provides increased space for fluids to be stored.

While the reservoir portion 207 and the placement portion 211 are shown with a specific shape, it should be understood that numerous shapes may be given to the delivery-and-fluid-storage bridge 202. For example, in another illustrative embodiment, the delivery- and storage bridge 202 is shaped like a triangle with the apex being the second longitudinal end. In another illustrative embodiment, the deliver-and-storage bridge 202 may have a shape that resembles a "lollipop"—a thinner section coming away from the first longitudinal end with a larger portion at the first longitudinal end.

Figure 10:
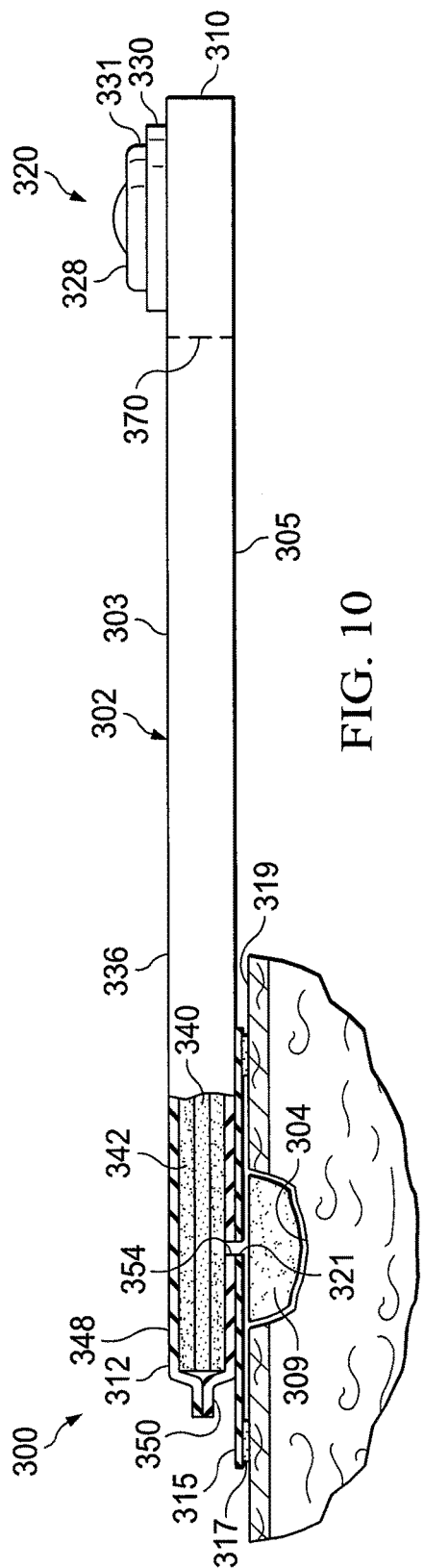
FIG. 10 is a schematic side view with a portion shown in cross section of a reduced-pressure treatment system utilizing a delivery-and-fluid-storage bridge.

Referring now primarily to FIG. 10, a reduced-pressure treatment system 300 is presented that is analogous in most respects to the reduced-pressure treatment system 100 of FIG. 1, and like or corresponding parts have been indicated by indexing the reference numerals by 200. A delivery-and-fluid-storage bridge 302 is used to deliver reduced pressure from a reduced-pressure source 320 to a treatment manifold 309 at the tissue site 304. The delivery-and-fluid-storage bridge 302 has a first side 303 and a second, patient-facing side 305.

The treatment manifold 309 is placed proximate the tissue site 304 and then a fluid seal is formed over the treatment manifold 309 by using a sealing member 315. An adhesive device 317 may be used to help form a fluid seal between the sealing member 315 and the patient's skin 319. The sealing member 315 may have a treatment aperture 321 for providing access to the treatment manifold 309. Thus, the reduced pressure is delivered through a second aperture 354 and through the treatment aperture 321 to the treatment manifold 309.

The delivery-and-fluid-storage bridge 302 has an encapsulation pouch 336 formed with a first encapsulation layer 348 and a second encapsulation layer 350. The encapsulation pouch 336 has disposed within an interior portion a plurality of delivery manifolds 342 and an absorbent layer 340.

Figure 11:
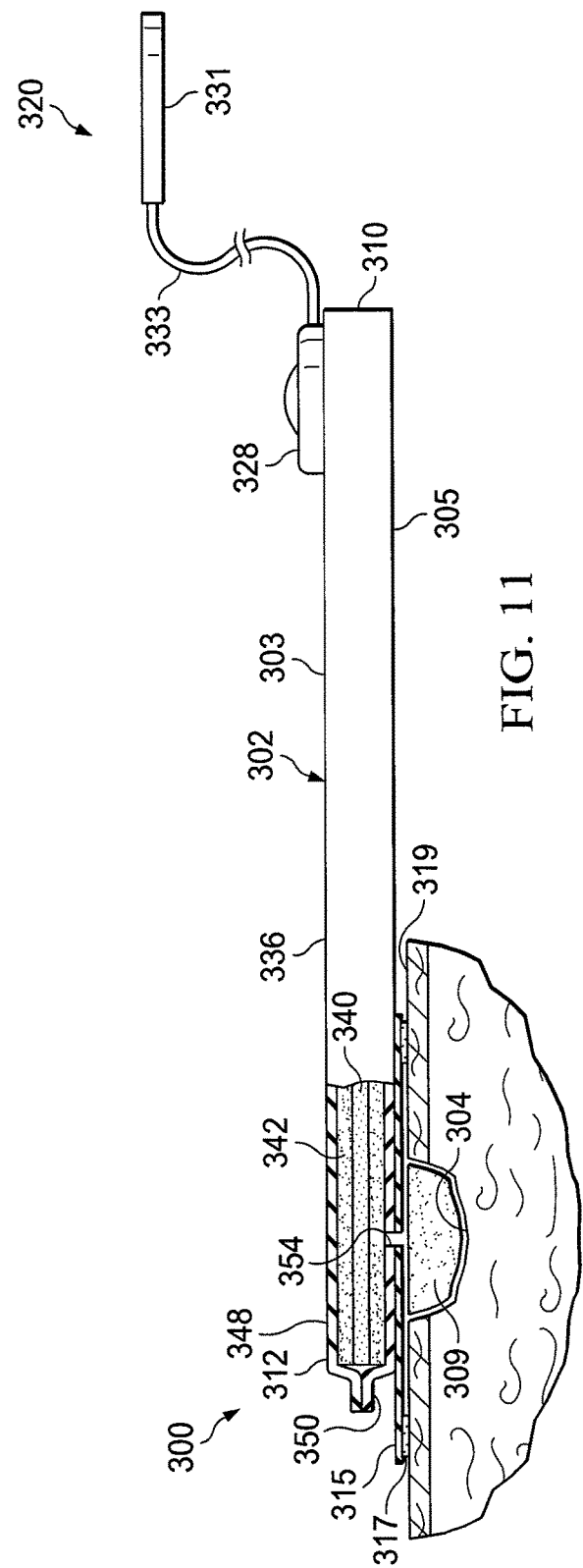
FIG. 11 is a schematic side view with a portion shown in cross section of an illustrative embodiment of a reduced-pressure treatment system.

A first aperture (not explicitly shown) is formed on the first longitudinal end 310. A reduced-pressure source 320 provides reduced pressure through the first aperture to the interior of the encapsulation pouch 336. From there, the reduced pressure is delivered to the second longitudinal end 312 as previously discussed. In this illustrative, non-limiting example, the reduced-pressure source 320 is a micro-pump 328, which has a piezoelectric pump 330 and a battery, such as battery 331, that are integrated with the delivery-and-fluid-storage bridge 302. In the illustrative embodiment of FIG. 11, the reduced-pressure source 320 is a micro-pump 328 with a piezoelectric pump 330 and the battery 331 is remote. The battery 331 is electrically coupled to the piezoelectric pump 330 by connector 333.

As shown in FIG. 10, the delivery-and-fluid-storage bridge 302 may include a separation portion 370, such as a thinned portion or perforations (with a two ply layer having displaced perforations in each to prevent leakage) of the encapsulation layers 348, 350 that facilitate removal of the first longitudinal end 310 of the delivery-and-fluid-storage bridge 302. The separation portion 370 is proximate the first longitudinal end 310, inboard of the reduced-pressure source 320. The separation portion 370 facilitates removal of the reduced-pressure source 320 so that the reduced-pressure source 320 or other components—the biological elements and electrical elements—may be disposed of separately from other portions of the delivery-and-fluid-storage bridge 302.

Figure 12:
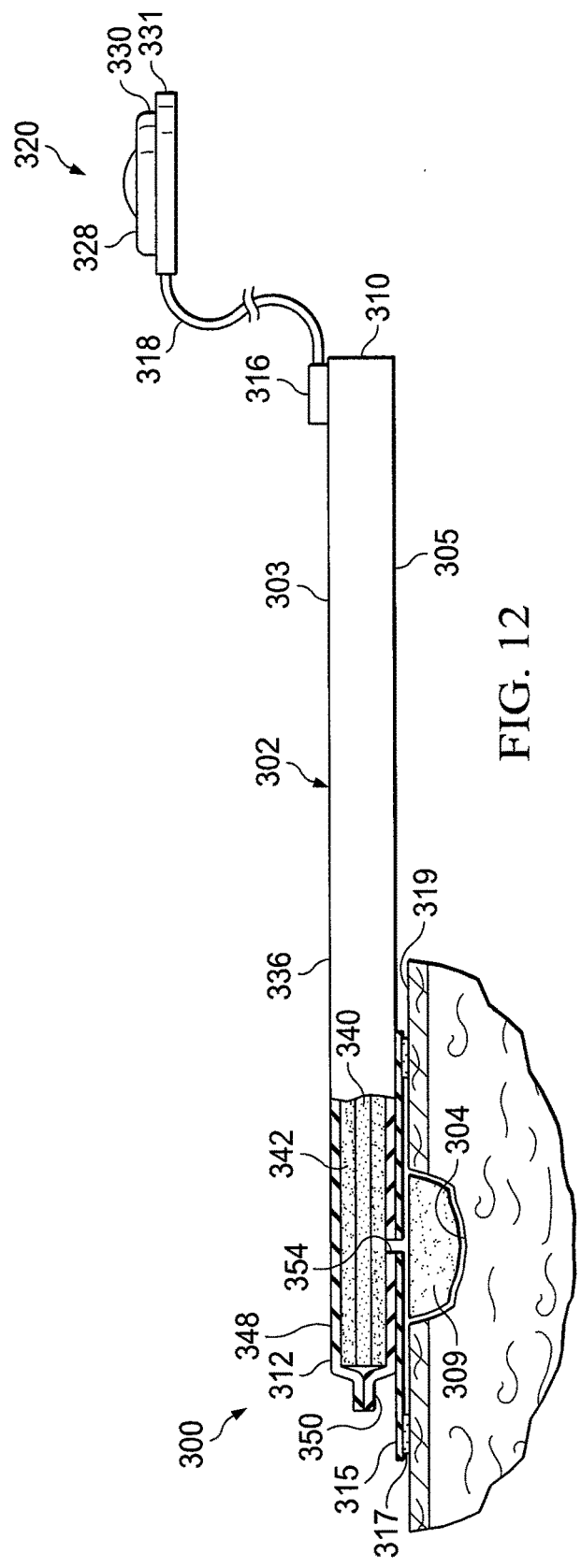
FIG. 12 is a schematic side view with a portion shown in cross section of an illustrative embodiment of a reduced-pressure treatment system.

In the illustrative embodiment of FIG. 12, the reduced-pressure source 320 is remote from the delivery-and-fluid-storage bridge 302 and a reduced-pressure delivery conduit 318 couples the reduced-pressure source 320 to a reduced-pressure interface 316 on the first longitudinal end 310 of the delivery-and-fluid-storage bridge 302. In this embodiment, the reduced-pressure source 320 may include a micro-pump 328. The micro-pump 328 may include a piezoelectric pump 330 and a battery 331. In some embodiments, the sealing member 315 may be omitted and the second, patient-facing side 305 of the delivery-and-fluid-storage bridge 302 may form the fluid seal over the treatment manifold 309.

The low profile of the delivery-and-fluid-storage bridges 102, 202, 302 herein allows for each bridge 102, 202, 302 to be used in numerous situations without raising pressure at a particular point, i.e., without causing a stress riser, which can lead to the formation of pressure ulcers. The delivery-and-fluid-storage bridge 102, 202, 302 separates liquids from gases. The liquids are drawn into the absorbent layer, e.g., absorbent layer 140, until saturation occurs and the gases are allowed to remain in the delivery manifolds 142 or manifold 138 from where the gases may be removed by a reduced pressure source.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A delivery-and-fluid-storage bridge, comprising:
   a delivery manifold extending along a length of the delivery-and-fluid-storage bridge for delivering reduced pressure through the delivery-and-fluid-storage bridge;
   an absorbent layer proximate the delivery manifold adapted to receive and store fluids, wherein the absorbent layer has an outer surface and an interior portion, the delivery manifold has an outer surface and an interior portion, and the outer surface of the delivery manifold is configured to be adjacent to the outer surface of the absorbent layer;
   a first encapsulating layer and a second encapsulating layer having an inner surface at least partially enclosing the delivery manifold and the absorbent layer;
   a first aperture formed proximate a first longitudinal end of the delivery-and-fluid-storage bridge for fluidly communicating reduced pressure to the delivery manifold from a reduced-pressure source;
   a second aperture formed proximate a second longitudinal end of the delivery-and-fluid-storage bridge for transmitting reduced pressure to a tissue site; and
   a conduit at the second longitudinal end of the delivery-and-fluid-storage bridge, the conduit being a lumen substantially isolated from fluid communication with the delivery manifold and the absorbent layer along the length of the delivery-and-fluid-storage bridge.

2. The delivery-and-fluid-storage bridge of claim 1, wherein the delivery manifold comprises a non-absorbent material and the absorbent layer comprises is a highly-absorbent material.

3. The delivery-and-fluid-storage bridge of claim 1, wherein the delivery manifold comprises a material with a plurality of flow channels that distribute fluids and the absorbent layer comprises at least one of the following: capillary-containing material, super absorbent fibers, hydrofibers, sodium carboxymethyl cellulose, alginate, and sodium polyacrylate.

4. The delivery-and-fluid-storage bridge of claim 1, further comprising an adhesive member proximate the second aperture.

5. The delivery-and-fluid-storage bridge of claim 1, wherein the absorbent layer comprises a capillary-containing material.

6. The delivery-and-fluid-storage bridge of claim 1, further comprising a hydrophobic filter proximate the first aperture for preventing fluids from exiting the delivery-and-fluid-storage bridge.

7. The delivery-and-fluid-storage bridge of claim 1, wherein the delivery-and-fluid-storage bridge has a reservoir portion with a plan view surface area $A_1$ and a placement portion with a plan view surface area $A_2$, and wherein $A_1 > A_2$.

8. The delivery-and-fluid-storage bridge of claim 1, wherein the first encapsulating layer and the second encapsulating layer are formed from an integral piece of polyurethane.

9. A delivery-and-fluid-storage bridge for use with a reduced-pressure treatment system, the delivery-and-fluid-storage bridge comprising:
   a plurality of delivery manifolds extending along a length of the delivery-and-fluid-storage bridge for delivering reduced pressure to a tissue site;
   an absorbent layer adapted to receive and absorb fluids, wherein the absorbent layer has an outer surface and an interior portion;
   wherein the absorbent layer is disposed between at least two delivery manifolds of the plurality of delivery manifolds;
   an encapsulating pouch encapsulating the plurality of delivery manifolds and the absorbent layer, the encapsulating pouch comprising:
      a first encapsulating layer and a second encapsulating layer having an inner surface at least partially enclosing the plurality of delivery manifolds and the absorbent layer, the second encapsulating layer comprising a patient-facing side of the delivery-and-fluid-storage bridge,
      a first aperture formed on the first encapsulating layer proximate a first longitudinal end of the delivery-and-fluid-storage bridge for fluidly communicating reduced pressure to the delivery manifolds from a reduced-pressure source, and
      a second aperture formed on the patient-facing side of the second encapsulating layer for transmitting reduced pressure to the tissue site and
   a conduit disposed within the encapsulating pouch and extending substantially along the length of the delivery-and-fluid-storage bridge.

10. The delivery-and-fluid-storage bridge of claim 9, wherein the absorbent layer comprises a capillary-containing material.

11. The delivery-and-fluid-storage bridge of claim 9, wherein the plurality of delivery manifolds comprises a plurality of foam members.

12. The delivery-and-fluid-storage bridge of claim 9, further comprising a micro-pump coupled to the first longitudinal end of the delivery-and-fluid-storage bridge.

13. The delivery-and-fluid-storage bridge of claim 9, further comprising a micro-pump coupled to the first longitudinal end of the delivery-and-fluid-storage bridge, wherein the micro-pump comprises a piezoelectric pump.

14. The delivery-and-fluid-storage bridge of claim 9, further comprising a micro-pump and a remote battery, the micro-pump coupled to the first longitudinal end of the delivery-and-fluid-storage bridge, wherein the micro-pump comprises a piezoelectric pump, and wherein the remote battery is coupled to the piezoelectric pump.

15. The delivery-and-fluid-storage bridge of claim 9, further comprising a micro-pump fluidly coupled to the first longitudinal end of the delivery-and-fluid-storage bridge, wherein the micro-pump comprises a piezoelectric pump, and wherein a remote battery is coupled to and proximate to the piezoelectric pump.

16. The delivery-and-fluid-storage bridge of claim 9, further comprising a separation portion formed proximate the first longitudinal end inboard of the first aperture.

17. The delivery-and-fluid-storage bridge of claim 9, further comprising an adhesive member proximate the second aperture on the patient-facing side of the delivery-and-fluid-storage bridge.

18. The delivery-and-fluid-storage bridge of claim 9, further comprising a hydrophobic filter proximate the first aperture.

19. The delivery-and-fluid-storage bridge of claim 9, wherein the delivery-and-fluid-storage bridge has a reservoir portion with a plan view surface area $A_1$ and a placement portion with a plan view surface area $A_2$, and wherein $A_1 > A_2$.

20. The delivery-and-fluid-storage bridge of claim 9, further comprising a wicking layer coupled to the patient-facing side of the second encapsulating layer.

21. The delivery-and-fluid-storage bridge of claim 9, further comprising an odor-control layer disposed within the encapsulating pouch.

22. The delivery-and-fluid-storage bridge of claim 9, wherein the conduit is substantially isolated from fluid communication with the plurality of delivery manifolds and the absorbent layer along the length of the delivery-and-fluid-storage bridge.

23. A method for treating a tissue site, the method comprising:
   providing a delivery-and-fluid-storage bridge, comprising:
      a delivery manifold extending along a length of the delivery-and-fluid-storage bridge, the delivery manifold comprising a first material,
      an absorbent layer proximate the delivery manifold adapted to receive and store fluids, the absorbent layer comprising a second material,
      wherein the absorbent layer has an outer surface and an interior portion, the delivery manifold has an outer surface and an interior portion, and the outer surface of the delivery manifold is configured to be adjacent to the outer surface of the absorbent layer, and
      an encapsulating pouch having an inner surface encapsulating the delivery manifold and the absorbent layer;
   placing a second longitudinal end of the delivery-and-fluid-storage bridge at the tissue site;
   applying a reduced pressure to a first longitudinal end of the delivery-and-fluid-storage bridge;
   communicating the reduced pressure through the delivery manifold to the tissue site through the second longitudinal end of the delivery-and-fluid-storage bridge;
   monitoring pressure proximate the tissue site through a conduit having an end positioned at the second longitudinal end of the delivery-and-fluid-storage bridge, the conduit disposed within the encapsulating pouch and being substantially isolated from fluid communication with the delivery manifold and the absorbent layer along the length of the delivery-and-fluid-storage bridge; and wicking liquids extracted from the tissue site through the second longitudinal end into the absorbent layer.

24. The method of claim 23, further comprising using an adhesive to fluidly seal the second longitudinal end of the delivery-and-fluid-storage bridge over the tissue site.

25. The method of claim 23, further comprising placing a treatment manifold proximate the tissue site; and placing a sealing member over the treatment manifold.

26. The method of claim 23, wherein applying a reduced pressure to the first longitudinal end comprises supplying reduced pressure from a reduced-pressure source to the first longitudinal end, and wherein there is no canister between the reduced-pressure source and the first longitudinal end.

27. The method of claim 23, wherein the absorbent layer comprises a capillary-containing material.

28. The method of claim 23, wherein the first material comprises a non-absorbent material and the second material comprises a highly-absorbent material.

29. The method of claim 23, wherein the first material comprises a material with a plurality of flow channels that distribute fluids and the second material comprises at least one of the following: capillary-containing material, super absorbent fibers, hydrofibers, sodium carboxymethyl cellulose, alginate, and sodium polyacrylate.

30. The method of claim 23, wherein wicking liquids extracted from the tissue site comprises wicking the liquids into the absorbent layer and storing substantially all the liquids received in the absorbent layer.

31. The method of claim 23, wherein wicking liquids extracted from the tissue site comprises wicking the liquids into the absorbent layer and storing substantially all the liquids received in the absorbent layer, and further comprising signaling when the absorbent layer is full.

32. A method of manufacturing a delivery-and-fluid-storage bridge, comprising:

providing a delivery manifold;

placing an absorbent layer proximate the delivery manifold, wherein the absorbent layer has an outer surface and an interior portion, the delivery manifold has an outer surface and an interior portion, and the outer surface of the delivery manifold is configured to be adjacent to the outer surface of the absorbent layer;

encapsulating the delivery manifold and the absorbent layer in an encapsulating pouch, the encapsulating pouch comprising a first encapsulating layer and a second encapsulating layer having an inner surface at least partially enclosing the delivery manifold and the absorbent layer, the second encapsulating layer comprising a second, patient-facing side of the delivery-and-fluid-storage bridge;

forming a first aperture proximate a first longitudinal end of the delivery-and-fluid-storage bridge for fluidly communicating reduced pressure to the delivery manifold from a reduced-pressure source;

forming a second aperture on the second, patient-facing side of the second encapsulating layer for transmitting reduced pressure to a tissue site; and disposing a conduit within the encapsulating pouch, wherein the conduit extends along a length of the delivery-and-fluid-storage bridge.

33. The method of manufacturing of claim 32, wherein the absorbent layer comprises a capillary-containing material.

34. The method of manufacturing of claim 32, wherein the delivery manifold comprises a plurality of foam members.

35. The method of manufacturing of claim 32, further comprising coupling a micro-pump to the first longitudinal end of the delivery-and-fluid-storage bridge.

36. The method of manufacturing of claim 32, further comprising coupling a micro-pump to the first longitudinal end of the delivery-and-fluid-storage bridge, wherein the micro-pump comprises a piezoelectric pump.

37. The method of manufacturing of claim 32, further comprising coupling a micro-pump to the first longitudinal end of the delivery-and-fluid-storage bridge, wherein the micro-pump comprises a piezoelectric pump, the method further comprising coupling a remote battery to the piezoelectric pump.

38. The method of manufacturing of claim 32, further comprising forming a separation portion of the delivery-and-fluid-storage bridge proximate the first longitudinal end and inboard of the first aperture.

39. The method of manufacturing of claim 32, further comprising applying an adhesive member proximate the second aperture on the patient-facing side of the delivery-and-fluid-storage bridge.

40. The method of manufacturing of claim 32, further comprising placing a hydrophobic filter proximate the first aperture.

41. The method of manufacturing of claim 32, wherein the delivery-and-fluid-storage bridge has a reservoir portion with a plan view surface area $A_1$ and a placement portion with a plan view surface area $A_2$, and wherein $A_1 > A_2$.

42. The method of manufacturing of claim 32, further comprising coupling a wicking layer to the second, patient-facing side of the second encapsulating layer.

43. The method of manufacturing of claim 32, further comprising disposing an odor-control layer within the encapsulated pouch.

44. The method of manufacturing of claim 32, wherein the conduit is substantially isolated from fluid communication with the delivery manifold and the absorbent layer along the length of the delivery-and-fluid-storage bridge.

45. The delivery-and-fluid-storage bridge of claim 1, wherein the conduit has an end positioned at the second longitudinal end of the delivery-and-fluid-storage bridge, and wherein the conduit extends substantially along the length of the delivery-and-fluid-storage bridge.

46. The delivery-and-fluid-storage bridge of claim 1, wherein the conduit is disposed between the first encapsulating layer and the second encapsulating layer and substantially isolated from fluid communication with the delivery manifold and the absorbent layer between the first longitudinal end and the second longitudinal end of the delivery-and-fluid-storage bridge.

47. The method of claim 23, further comprising determining a fluid saturation level within the delivery-and-fluid-storage bridge based upon a comparison of the reduced pressure applied to the first longitudinal end with a pressure monitored proximate the tissue site, wherein the pressure monitored proximate the tissue site is monitored at the second longitudinal end of the delivery-and-fluid-storage bridge.

48. The method of claim 23, further comprising determining a fluid saturation level within the delivery-and-fluid-storage bridge based upon a comparison of the reduced pressure applied to the first longitudinal end with a pressure monitored proximate the tissue site, wherein the pressure monitored proximate the tissue site is monitored at the tissue site.

49. The method of claim 23, further comprising comparing the reduced pressure applied to the first longitudinal end with a pressure monitored proximate the tissue site by the conduit.

50. A delivery-and-fluid-storage bridge, comprising:
a delivery manifold extending along a length of the delivery-and-fluid-storage bridge;
an encapsulating pouch having an inner surface enclosing the delivery manifold;
a first aperture proximate a first longitudinal end of the delivery-and-fluid-storage bridge;
a second aperture proximate a second longitudinal end of the delivery-and-fluid-storage bridge; and
a conduit at the second longitudinal end of the delivery-and-fluid-storage bridge, the conduit being substantially isolated from fluid communication with the delivery manifold along the length of the delivery-and-fluid-storage bridge, wherein the conduit is configured to be disposed at or near a tissue site at the second longitudinal end of the delivery-and-fluid-storage bridge.

51. The delivery-and-fluid-storage bridge of claim 50, wherein the conduit extends substantially along the length of the delivery-and-fluid-storage bridge.

52. The delivery-and-fluid-storage bridge of claim 50, wherein the conduit is disposed within the encapsulating pouch.

53. The delivery-and-fluid-storage bridge of claim 50, wherein the delivery manifold comprises a porous material adapted to communicate fluid.

54. The delivery-and-fluid-storage bridge of claim 50, further comprising an absorbent layer proximate the delivery manifold adapted to receive and store fluids, wherein the encapsulating pouch is adapted to enclose the delivery manifold and the absorbent layer.

55. The delivery-and-fluid-storage bridge of claim 54, wherein the conduit is substantially isolated from fluid communication with the delivery manifold and the absorbent layer along the length of the delivery-and-fluid-storage bridge.

56. The delivery-and-fluid-storage bridge of claim 54, wherein the delivery manifold comprises a non-absorbent material and the absorbent layer comprises a highly-absorbent material.

57. The delivery-and-fluid-storage bridge of claim 50, wherein the encapsulating pouch comprises a first encapsulating layer and a second encapsulating layer enclosing the delivery manifold.

58. The delivery-and-fluid-storage bridge of claim 57, wherein the first aperture is formed on the first encapsulating layer.

59. The delivery-and-fluid-storage bridge of claim 57, wherein the second aperture is formed on a second, patient-facing side of the second encapsulating layer.

60. The delivery-and-fluid-storage bridge of claim 50, wherein the first aperture is proximate the delivery manifold.

61. The delivery-and-fluid-storage bridge of claim 50, wherein the conduit has an end disposed at the second longitudinal end of the delivery-and-fluid-storage bridge.

62. The delivery-and-fluid-storage bridge of claim 50, wherein the first aperture is adapted to be fluidly coupled to a reduced-pressure source and the second aperture is adapted to be fluidly coupled to a tissue site.

63. A delivery-and-fluid-storage bridge, comprising:
a first manifold having an outer surface an interior portion extending along a length of the delivery-and-fluid-storage bridge;
a second manifold having an outer surface and interior portion;
an encapsulating pouch having an inner surface enclosing the first manifold and the second manifold;
a first aperture proximate a first longitudinal end of the delivery-and-fluid-storage bridge;
a second aperture proximate a second longitudinal end of the delivery-and-fluid-storage bridge; and
a longitudinal sheet disposed within the encapsulating pouch between the first manifold and the second manifold.

64. The delivery-and-fluid-storage bridge of claim 63, wherein the encapsulating pouch comprises a first encapsulating layer and a second encapsulating layer, and wherein the longitudinal sheet is coupled to at least a portion of the first encapsulating layer and at least a portion of the second encapsulating layer.

65. The delivery-and-fluid-storage bridge of claim 63, wherein at least a portion of the inner surface of the encapsulating pouch and the longitudinal sheet define a conduit having a lumen.

66. The delivery-and-fluid-storage bridge of claim 65, wherein the second manifold is disposed within the lumen.

* * * * *

UNITED STATES PATENT AND TRADEMARK OFFICE
CERTIFICATE OF CORRECTION

PATENT NO. : 10,279,088 B2  
APPLICATION NO. : 14/334510  
DATED : May 7, 2019  
INVENTOR(S) : Tim Robinson Page 1 of 2

It is certified that error appears in the above-identified patent and that said Letters Patent is hereby corrected as shown below:

On the Title Page

<u>On Page 5, Column 2, Under (Other Publications)</u>  
Line 29, delete "Internationl" and insert -- International --, therefor.  
Line 29, delete "Internationl" and insert -- International --, therefor.  
Line 32, delete "Internation" and insert -- International --, therefor.

<u>Page 6, Column 1, Under (Other Publications)</u>  
Line 3, delete "Terapy" and insert -- Therapy --, therefor.  
Line 24, delete "Internationl" and insert -- International --, therefor.  
Line 42, delete "PCT/U52015/" and insert -- PCT/US2015/ --, therefor.  
Line 44, delete "PCT/U52015/" and insert -- PCT/US2015/ --, therefor.  
Line 50, delete "Intemational" and insert -- International --, therefor.

<u>Page 7, Column 1, Under (Other Publications)</u>  
Line 17, delete "Hypermia" and insert -- Hyperemia --, therefor.

In the Specification

<u>Column 3</u>  
Line 46, delete "of the of the" and insert -- of the --, therefor.

<u>Column 10</u>  
Line 38, delete "ration" and insert -- ratio --, therefor.  
Line 51, delete "delivery- and storage" and insert -- delivery-and-fluid-storage --, therefor.  
Lines 53-54, delete "deliver-and-storage" and insert -- delivery-and-fluid-storage --, therefor.

Signed and Sealed this  
Twentieth Day of July, 2021

Drew Hirshfeld  
*Performing the Functions and Duties of the  
Under Secretary of Commerce for Intellectual Property and  
Director of the United States Patent and Trademark Office*

In the Claims

Column 14
Line 17, in Claim 16, after "end" insert -- and --.